United States Patent [19]
Thomas

[11] 4,366,817
[45] Jan. 4, 1983

[54] WINGED IV CATHETER

[75] Inventor: Joseph J. Thomas, Berwyn, Pa.

[73] Assignee: Burron Medical Inc., Bethlehem, Pa.

[21] Appl. No.: 266,970

[22] Filed: May 26, 1981

[51] Int. Cl.³ .............................................. A61N 5/00
[52] U.S. Cl. ...................................... 604/174; 604/53
[58] Field of Search ............ 128/349 R, 214 R, 214.4, 128/221, 348, DIG. 16

[56] References Cited
U.S. PATENT DOCUMENTS

| 3,463,152 | 8/1969 | Sorenson | 128/214.4 |
| 3,537,451 | 11/1970 | Beck et al. | 128/214.4 |
| 3,589,361 | 6/1971 | Loper et al. | 128/214.4 |
| 3,769,975 | 11/1973 | Nimoy et al. | 128/214.4 |
| 3,906,946 | 9/1975 | Nordstrom | 128/214.4 |
| 4,177,809 | 12/1979 | Moorehead | 128/DIG. 16 |
| 4,194,504 | 3/1980 | Harns et al. | 128/DIG. 16 |

Primary Examiner—Stephen C. Pellegrino
Attorney, Agent, or Firm—Shoemaker and Mattare, Ltd.

[57] ABSTRACT

A catheter anchoring assembly includes a winged section which is easily anchored to a patient to securely attach the assembly to that patient. The winged section includes a tubular body attachable to a catheter hub and through which the catheter extends. The winged section extends beyond a stem on the catheter hub and is larger than the outer diameter of the catheter tube whereby kinking of that catheter tube is prevented. The tubular body can be tilted with respect to the wing of the winged section.

6 Claims, 5 Drawing Figures

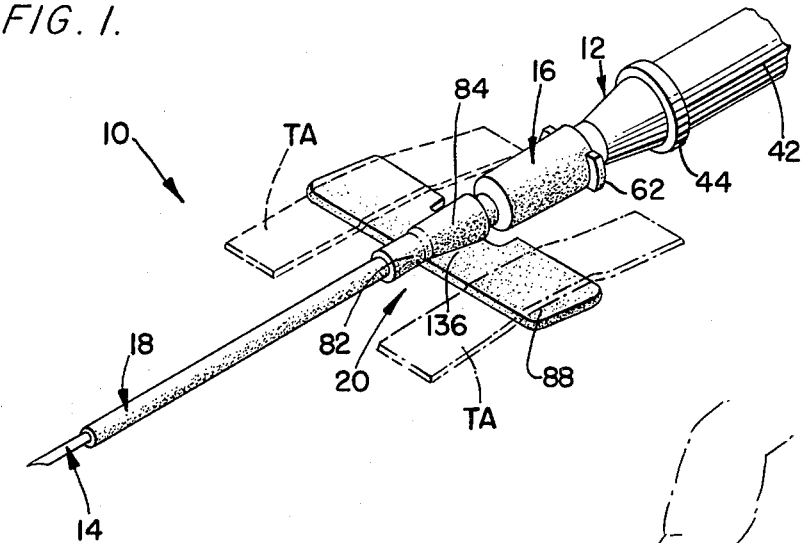
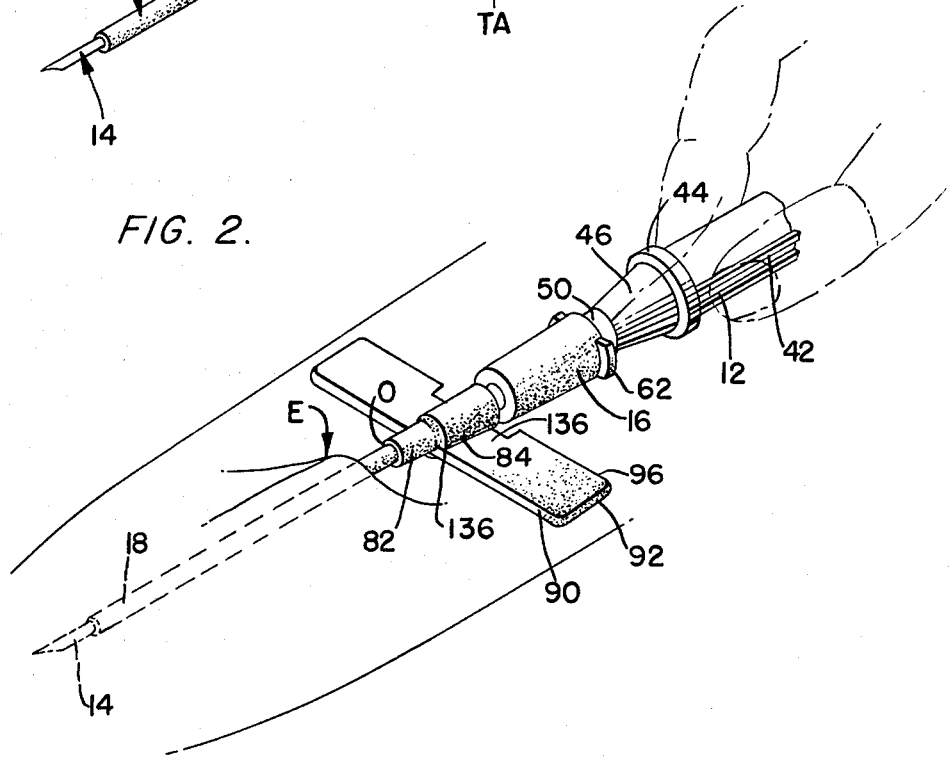
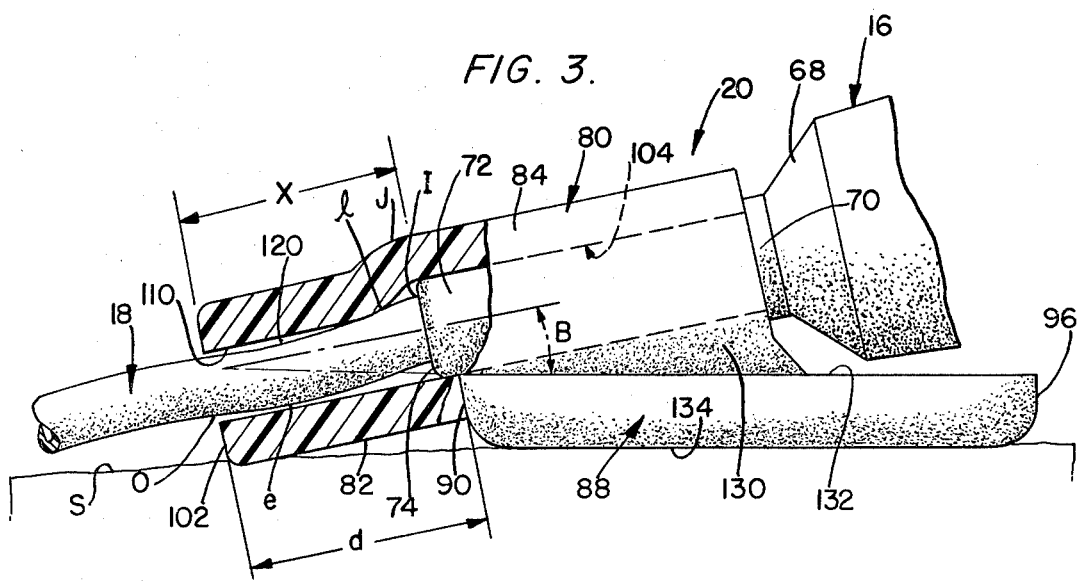

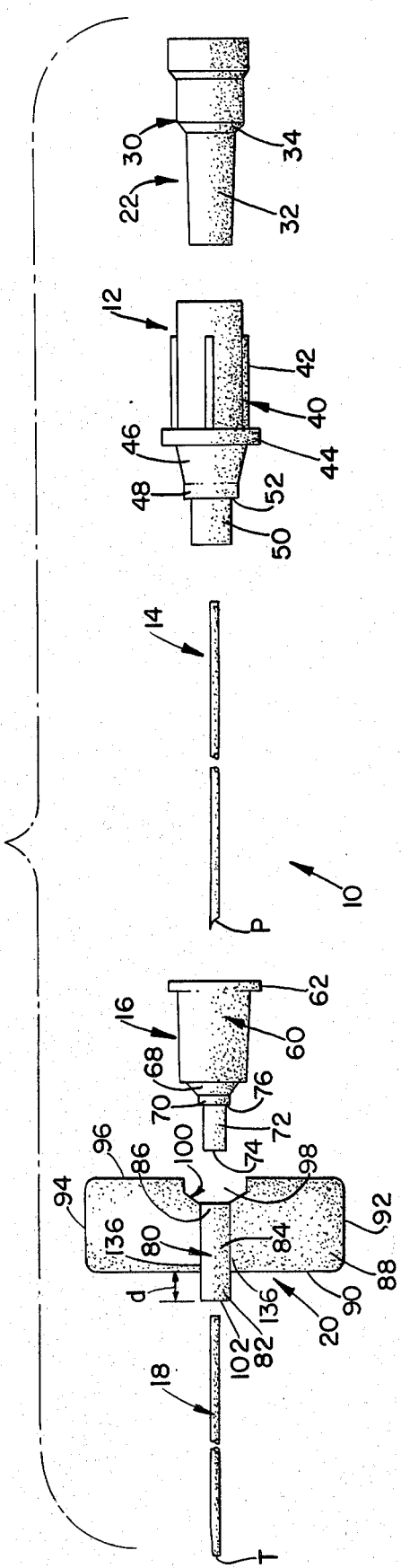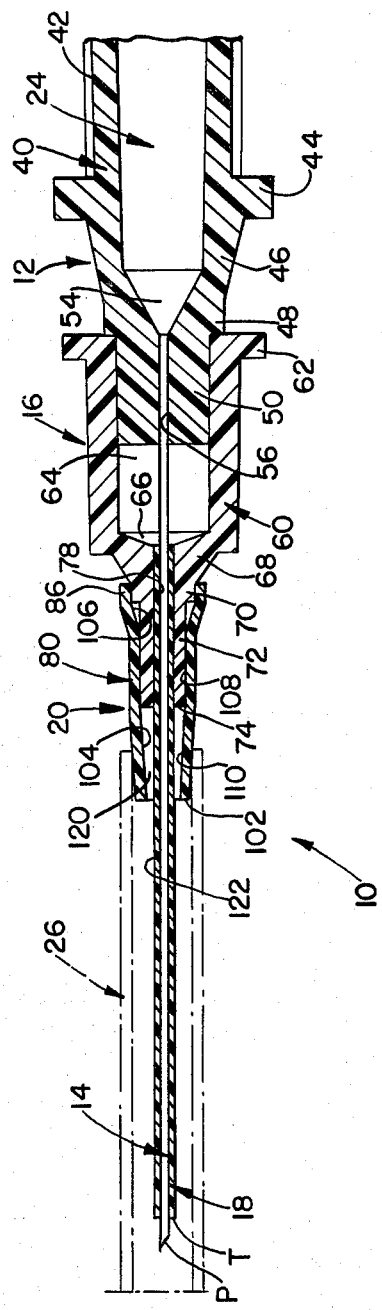

WINGED IV CATHETER

BACKGROUND OF THE INVENTION

The present invention relates, in general, to catheter assemblies, and, more particularly, to catheter anchoring assemblies.

Assemblies used to anchor a catheter to a patient during administration of intravenous fluids to that patient have been subject to several drawbacks. These assemblies were often difficult to attach to the patient, and once attached, were subject to movement if the patient moved. This problem was especially onerous if the patient was small, such as a child.

This difficulty engendered anchoring devices intended to quickly and securely attach a catheter to a patient. Examples of such anchoring devices are shown in U.S. Pat. Nos. 4,161,177, 4,194,504, and 4,198,973, wherein wings are provided and are taped to a patient.

While these known devices do alleviate the anchoring problem somewhat, they are not entirely successful and are still somewhat difficult to manipulate. However, even more important than the above drawback to known catheter anchoring assemblies, these devices do not approach a second significant drawback inherent in such devices. This second problem involves kinking of the catheter tube if the patient moves.

Kinking, as used herein, involves the bending of a catheter tube. This kinking may be sufficient to restrict the flow of IV fluid, or possibly shut off such IV fluid flow altogether. It is evident that kinking to any significant degree may be dangerous to the patient, and certainly inhibits any treatment administered due to the interruption of the desired IV administration.

The kinking problem can be overcome somewhat by the addition of materials to the catheter tube which are intended to stiffen the tube and help that tube resist kinking. However, such tube property changes cannot be significant enough to obviate the kinking problems due to other considerations involved in such elements.

The kinking problem is especially significant in small catheters, such as might be used on small children. Small children are the patients most likely to move enough to create a catheter kinking problem, thereby exacerbating the problem.

Accordingly, there is need for a device which is easily manipulated by a nurse, or other such personnel, and securely anchors a catheter tube on a patient while preventing kinking of the catheter tube.

SUMMARY OF THE INVENTION

The device embodying the teachings of the present invention is easily placed on a patient and prevents kinking of a catheter tube.

The device includes a wing section having a wing which is secured to a patient. The wing section includes a tubular body having a bore therethrough which receives a catheter hub stem at one end of the body, with the other end of the body extending beyond the end of that stem. The tubular body has an inner diameter larger than the outer diameter of the catheter tube. The body can also be canted with respect to the wing at an angle corresponding to the angle assumed by the catheter with respect to the patient's skin surface during venipuncture so the catheter does not bend when anchored to the patient.

Any bending of the catheter tube thus causes that tube to contact the wing section tubular body. This contact occurs at locations spaced from the intersection of the catheter tube and the catheter hub. Any bending of the catheter tube is thus distributed along a distance thereof corresponding to the length the tubular body extends beyond the catheter hub stem and is limited by the size of the annular gap defined between the tubular body inner surface and the catheter tube outer surface. Thus, any bending of the catheter tube is gentle at any particular location and will not be sharp enough to kink that tube, thus preventing or interrupting the IV fluid flow to a patient.

The device embodying the teachings of the present invention thus has a wing section which solves two problems inherent with known catheter anchoring assemblies, to-wit: secure stable anchoring; and prevention of flow interrupting kinks in the catheter tube.

The tubular body can be raised to be distally declining so that the catheter does not have to bend to fluidly connect a patient's vein to a tube of the IV setup. Such inclination further contributes to the kink preventing feature of the device of the present disclosure.

Thus, the wing facilitates taping to the skin which provides greater stabilization than that which could be achieved by wrapping tape around a catheter hub directly and then onto the skin. In addition, greater patient comfort is achieved.

The wing section is molded separately, which allows freedom of choice of material (it is desirable to have a wing section which is more flexible than the catheter hub). However, after force fitting the wing over the catheter hub, stabilization is achieved as though the assembly were monolithic.

The distal end of the central cylindrical section of the wing body projects beyond the end of the distal end of the catheter hub. This section, by virtue of its flexibility, provides a cushion which relieves stresses as the catheter tube is bent. Thus, this wing design imparts great resistance to kinking of a catheter tube.

OBJECTS OF THE INVENTION

It is a main object of the present invention to prevent kinks in a catheter tube.

It is another object of the present invention to anchor a catheter tube to a patient in a stable and secure manner.

It is yet another object of the present invention to easily and quickly anchor a catheter tube to a patient in a stable and secure manner.

It is still another object of the present invention to anchor a catheter tube to a patient in a manner which does not require the catheter tube to bend.

These together with other objects and advantages which will become subsequently apparent reside in the details of construction and operation as more fully hereinafter described and claimed, reference being had to the accompanying drawings forming part hereof, wherein like reference numerals refer to like parts throughout.

BRIEF DESCRIPTION OF THE DRAWINGS

FIG. 1 is a perspective showing a catheter anchoring assembly embodying the teachings of the present invention.

FIG. 2 is a perspective showing a step in a veni-puncture procedure using the device embodying the teachings of the present invention.

FIG. 3 is a partially cut away side elevation showing a canted wing section wherein is illustrated the extension of a wing section tube beyond the end of a catheter hub stem and a gap between a catheter tube and a wire defining a bore through the wing section tube.

FIG. 4 is an exploded view showing the device embodying the teachings of the present invention.

FIG. 5 is an assembled view of the device embodying the teachings of the present invention with the wing section shown edge-on for the sake of clarity.

DETAILED DESCRIPTION OF THE INVENTION

Shown in FIG. 1 is a catheter assembly 10 for use with an IV setup to administer IV fluids, or the like, to a patient. The assembly 10 has structure which significantly reduces, if not completely eliminates, the possibility of a catheter tube kinking due to patient movement, or the like, while also providing means for stabilizing the assembly on the patient.

As best shown in FIGS. 4 and 5, the assembly 10 includes a needle hub 12 on which is mounted an introducer needle 14, a catheter hub 16 on which is mounted a catheter tube 18 and a wing section 20. The details of each of these units will be presented and discussed below. A flash plug 22 is shown in FIG. 4 and is received in a flash chamber 24 of the needle hub 12. A sheath 26 protects the catheter and introducer needle prior to use thereof. The assembled catheter assembly is shown in FIGS. 1, 2 and 5.

It is to be noted that the elements 12-22, along with the sheath 26, are unitary and are formed in suitable processes, such as molding, or the like. The elements will be discussed in parts for the sake of clarity, but are integral elements in practice.

As best shown in FIG. 4, the flash plug 22 includes a stepped body 30 having a tubular prow section 32 integral therewith. A longitudinal bore is defined through the plug 22 through which fluid flows. Preferably, the plug 22 is formed of high density polyethylene, or the like. The prow 32 is received in flash chamber 24, which is tapered longitudinally of the needle hub 12 and has an inner diameter sized to frictionally engage the flash plug prow 32 in a manner which holds the flash plug securely engaged with the needle hub. A shoulder 34 on the plug engages a rear end of the needle hub to define the limit of the insertion of the prow into the flash chamber 24.

As shown in FIG. 5, the needle hub includes a tubular body 40 having elongate tongues 42 on the external surface thereof and an annular collar 44 surrounding that body. A forward section of the needle hub includes a trunk section which has a frusto-conical base 46 and a tubular cap 48 integral with and extending forwardly of the frustum of the trunk base. A tubular nose section 50 is integral with and extends forwardly of the tubular cap. The outer diameter of the nose is less than the outer diameter of the tubular cap so a shoulder 52 is formed at the intersection of these two elements.

As best shown in FIG. 5, the flash chamber includes a conical converging (in the right-to-left direction of FIG. 5) portion 54 fluidly connected to a cylindrical bore 56 which extends from the apex of the conical portion 54 longitudinally through the hub trunk section. The introducer needle 14 is affixed to the needle hub in this bore 56 and extends forwardly from this hub trunk section so the needle piercing point P is spaced from the cather hub a suitable distance as required for proper IV techniques. Preferably, the needle hub is formed of polypropylene, or the like.

The catheter hub 16 is also shown in FIG. 5 to be unitary and to include a tubular body 60 having a collar 62 surrounding an aft end thereof. A bore 64 extends longitudinally through the hub and has a conical converging (in the direction of IV fluid flow) section 66 at a forward end thereof. A forward portion of the hub includes a frusto-conical trunk section 68 having a tubular cap section 70 integral therewith and extending forwardly of the trunk section. A tubular stem 72 extends forwardly of the cap section and has a fore end 74 spaced from the cap 70. The outer diameter of the stem is less than the outer diameter of the cap 70 so a shoulder 76 is defined at the intersection of the stem and the cap. A cylindrical bore 78 is defined to extend from the apex of the converging section 66 through the catheter hub trunk section to be co-linear with the longitudinal centerline of the bore 64 and with the introducer needle 14 when the catheter hub is attached to the needle hub as shown in FIG. 5.

The catheter tube 18 is securely affixed to the catheter hub 16 in the bore 78, and extends forwardly of the hub 16 for a distance suitable for proper IV techniques. As shown in FIG. 5, introducer needle piercing point P extends beyond tip T of the catheter tube. As is shown in FIG. 4, the distal end of the catheter tube is distally tapered so the inner diameter of that tube at the tip T approximates the outer diameter of the introducer needle to facilitate proper veni-puncture and proper catheter tube setting.

As best shown in FIG. 4, wing section 20 includes tubular body 80 having a forward portion 82, a rear portion 84 and a lead-in section 86. The body 80 is mounted on a wing 88 which is generally rectangular in shape and has a forward edge 90, side edges 92 and 94, and a rear edge 96 with a notch 98 defined in that rear edge. The notch includes stepped sides 100 which are shaped to accommodate the trunk section of the catheter hub 16. The body forward and rear portions are divided by forward edge 90. In reality, these portions form one continuous body portion 80. The two sections are not physically distinct from each other and division of the body 80 into a forward and a rear portion is done only for the sake of explanation of the structure, function and operation of the invention. The forward portion 82 extends forwardly of and beyond the wing forward edge 90 for a predetermined distance d to forward tip 102 of the body. The length of the distance d is determined according to constraints and results as will be apparent from the teaching of this disclosure. Based on the guidance provided by such teaching and on his own knowledge, one skilled in the art can readily determine the dimensions of distance d.

As best shown in FIG. 5, the body 80 has a bore 104 defined therethrough. The body has an essentially constant wall thickness so the bore 104 is shaped to correspond to the shape of that body thereby including a lead-in section 106, a rear section 108 and a forward section 110. As above, bore 104 is continuous from the lead-in section to the outer tip 102, with the bore forward and rear sections being designated as such for the sake of convenient explanation. The bore is sized so that the diameter of the bore section 108 is less than the outer diameter of the catheter hub stem 72 so the tubular body tapers inwardly toward the tip 102 thereof.

The diameter of bore 104 is selected to correspond to the outer diameter of the catheter hub cap 70 at the lead-in section 106 so the bore snugly engages that cap, and, as above-discussed, to be slightly smaller than the outer diameter of the catheter hub stem 72 so that stem is snugly engaged in the bore rear section and the tubular body tapers inwardly from the tip 74 of the catheter hub stem to the tip 102 of the tubular body.

As shown in FIG. 3, when part of the tubular body is supported, the taper shown in FIG. 5 is transformed into a discontinuity J. However, in either situation, the diameter of the bore 104 is less than the outer diameter of the catheter hub stem and greater than the outer diameter of the catheter tube 18.

As shown in FIG. 5, the inner diameter of the bore forward section 110 is greater than the outer diameter of the catheter tube 18 so an annular gap 120 is defined between outer surfaces 122 of the catheter tube and the inner surface of the tube body 80.

The inner diameter of the bore 110 is selected so the size of the gap 120 is determined according to guidelines similar to those associated with the selection of the distance d. These guidelines will be apparent from the following discussion of the operation and function of the distance d and the gap 120.

As shown in FIG. 3, the wing section includes a riser section 130 mounting the tubular body 80 onto top surface 132 of the wing 88. The top surface 132 is planar and the wing 88 also includes a planar undersurface 134. As indicated in FIGS. 2 and 4, portions 176 immediately adjacent the body 80 are flexible enough to permit upfolding of the wing. As is evident to those skilled in the art, such upfolding facilitates final catheter placement after successful veni-puncture. It is noted that the wings are not used until after successful veni-puncture. The riser section is distally declining at an angle B. This angle is selected to correspond to the angle formed between the surface S of the patient's skin and the catheter after veni-puncture, so that after mounting, the catheter tube assumes an essentially straight line configuration. Were it not for angle B, the catheter tube would have to deflect to permit the catheter tube to connect the catheter to the IV set tubing. Angle B is selected according to the constraints of comfortable use and anchoring, as well as the other criteria known to those skilled in the art. It is noted that the benefits connected with this feature are obtained after the needle 14 is removed. Preferably, angle B is about 12°, but can be any other angle suitable and desirable to such skilled artisans.

Insertion is indicated in FIG. 2, and after such procedure, the wing 88 is placed on the patient's skin and detachably anchored thereto by a hold-down means, such as tape TA, or the like. The angle B helps define the straight line configuration shown in FIG. 1 for the assembly 10. The wing section 20 thus serves to stabilize the catheter assembly 10 on a patient and prevent inadvertent removal of the catheter.

The purpose of the distance d and the gap 120 will now be discussed with reference to FIGS. 3 and 5.

As shown in these figures, distance d is selected so the tubular body 80 extends beyond tip 74 of the catheter hub a distance x. The gap 120 is selected as a function of distance x so the catheter will thus contact the tubular body, as, for example, at location e proximally adjacent tip 102 of the tubular body and/or at location l distally adjacent tip 74 of the catheter hub prior to undergoing any deflection at intersection I between the catheter tube 18 and the tip 74 of the catheter hub stem section 72.

As shown in FIG. 3, the contact between the catheter tube and the tubular body at locations e and l result in a gentle bending of the catheter tube; whereas, a bend occurring at intersection I is likely to be sharp enough to kink the catheter tube. Such catheter tube kinking as is likely to occur at location I will reduce the flow of IV fluid through the catheter tube, and hence to the patient. Such reduction may be significant or complete, depending on the severity of the kink occurring in the catheter tube.

The bends in the catheter tube occurring at the locations distally forward of the location I as defined by extension X of the tube 80 beyond tip 74 of the catheter hub stem 72 are not likely to create such a significant reduction in IV fluid flow through the catheter tube because gap 120 and distance d are selected so the tube 18 will contact the wall of the tube 80 prior to undergoing a bend severe enough to restrict the flow area of the tube 18 significantly, or at all. Any bends in tube 18 can be kept gentle enough to prevent any flow restriction in the tube 18.

The catheter assembly 10 is shown in FIG. 2 to be placed close to the entrance site E in the patient's skin. This close proximity of the entrance site plus the angle B prevent the catheter tube from being bent at location O distally adjacent the tip 102 of the tube 80. Thus, there is little, if any, likelihood that the tube 18 will become kinked between the tube 80 and the entrance site E.

Element lengths, distances and other dimensions of the various elements described above are thus not restricted to the values presented herein. It is only required that tubular body 80 extend beyond tip 74 of the catheter hub stem 72 and be sized to loosely receive the catheter tube therethrough, while leaving a gap 120 between the inner wall of that body and the catheter tube.

Preferably, the wing is about one inch long as measured between side edges 92 and 94 and about 0.375 inches wide as measured between front edge 90 and rear edge 96. The overall dimensions of one inch by 0.375 inches are deemed to be optimum to provide ample area for taping to the skin, yet not result in excessive bulk. The dimensions allow, together with the flexibility of the material, conformance to irregular surfaces of the human body, including wrapping around the limb of an infant. However, these dimensions are not intended as restrictions.

The material of construction deemed to be optimum from the standpoint of patient comfort, conformability, elastic properties and practicality in molding is Kraton Thermoplastic elastomer (TM of Union Carbide Corp.). A silicone rubber or a natural latex would also provide the desired end properties, but would not be as economical to produce. The properties of a rubber or thermoplastic elastomer are necessary (as opposed to soft or hard plastic).

The 12° angle of the tubular body relative to the top surface of the wing provides direction of the catheter tubing through the skin, tissue and vein wall. That is, the canting of the tubular body lifts the proximal end of the catheter tubing which is attached to the hub, relative to the skin, thus keeping the catheter tube as straight as is possible which is a further safety factor against kinking. This angle is deemed to be optimum, but the scope of this invention will still be realized if the angle were in a range of 0° to 30°.

The length of the cylindrical section 82 is preferably 0.375 inches and is critical from the standpoint that it must be long enough to provide sufficient area for mechanical attachment to the catheter hub. As above discussed, the inner diameter of this section is smaller than the outer diameter of the stem of the catheter hub which provides an interference fit. However, in order to achieve security, it is preferred that the interference fit exists over approximately ¼ inch of length in the preferred embodiment. It is important that this tubular body project the distance d beyond the end of the hub; it is this projection d which provides the cushion for the catheter tubing if that tubing is subject to bending. The minimum length for this projection is judged to be approximately 3/32 inches. In the preferred embodiment, the catheter outer diameter is approximately 0.030 inches and the inner diameter of the central cylindrical section is 0.040 inches. This allows bending of the tube by approximately 0.005 inches in the radial direction prior to contact with the central cylindrical section, which is the cushion for the tube. This amount of deflection is not harmful to the tube and doe not impose a stress on the cushion. It is desirable not to impose a stress on the cushion until absolutely necessary.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:

1. A catheter tube anchoring means comprising:
   a catheter tube, said catheter tube having an outer surface;
   catheter tube supporting means having a stem out of which said catheter extends, said stem having a forward tip thereon; and
   a wing section mounted on said catheter tube supporting means and including an elongate tubular body having a bore therethrough, said stem being engaged in one end of said bore and said catheter tube extending through said bore, said body extending beyond said stem forward tip to define a catheter tube kink preventing section on said body, said bore having an inner cross-sectional size greater than the cross-sectional size of said catheter tube outer surface to define a catheter tube kink preventing gap between said catheter tube and said body,
   said body kink preventing section and gap preventing said catheter tube from bending at any one location thereon to a degree sufficient to significantly interrupt flow of fluid through said catheter tube.

2. The catheter tube anchoring means defined in claim 1 further including an introducer needle and a needle supporting means connected to said catheter supporting means.

3. The catheter tube anchoring means defined in claim 2 further including a flash plug connected to said needle supporting means.

4. The catheter tube anchoring means defined in claim 1 wherein said wing section further includes a planar, polygonal wing.

5. The catheter tube anchoring means defined in claim 4 wherein said wing section further includes a riser section connecting said tubular body to said planar wing, said riser section being distally declining of said elongate body.

6. The catheter tube anchoring means defined in claim 5 wherein said riser section is angled with respect to said planar wing sufficiently to ensure a straight line orientation of said catheter tube after veni-puncture and after said wing section is anchored to a patient.

* * * * *